United States Patent [19]

Kremer

[11] Patent Number: 5,478,951
[45] Date of Patent: Dec. 26, 1995

[54] METHOD FOR THE PURIFICATION OF 23-E ISOMERS OF 23-IMINO DERIVATIVES OF LL-F28249 COMPOUNDS

[75] Inventor: Kenneth A. M. Kremer, Lawrenceville, N.J.

[73] Assignee: American Cyanamid Company, Madison, N.J.

[21] Appl. No.: 263,967

[22] Filed: Jun. 22, 1994

[51] Int. Cl.⁶ .................................................. C07D 315/00
[52] U.S. Cl. .................................................. 549/264
[58] Field of Search .......................................... 549/264

[56] References Cited

U.S. PATENT DOCUMENTS

| | | | |
|---|---|---|---|
| 4,916,154 | 4/1990 | Asato et al. | 514/450 |
| 4,988,824 | 1/1991 | Maulding et al. | 549/264 |

*Primary Examiner*—C. Warren Ivy
*Assistant Examiner*—Amelia Owens
*Attorney, Agent, or Firm*—Peggy A. Climenson

[57] ABSTRACT

The present invention provides a method for the purification of a 23-E isomer of a 23-imino derivative of a LL-F28249 compound having the structural formula I

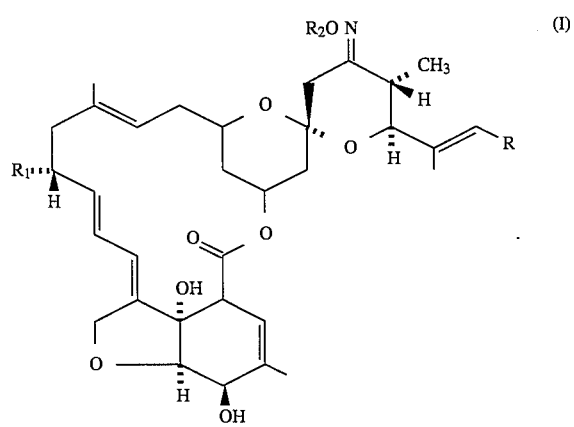

18 Claims, No Drawings

METHOD FOR THE PURIFICATION OF 23-E ISOMERS OF 23-IMINO DERIVATIVES OF LL-F28249 COMPOUNDS

BACKGROUND OF THE INVENTION

23-Imino derivatives of LL-F28249 compounds, their preparation and use are described in U.S. Pat. No. 4,916,154. Those compounds are particularly useful for preventing or controlling helminth, ectoparasite, insect and acarid infestations in human and animal health areas.

Various formulations of the 23-E isomer of the 23-(O-methyloxime) of LL-F28249alpha are used worldwide. When preparing those formulations, it is highly desirable to use high purity technical material. However, arduous and time-consuming methods are currently used to increase the purity of technical material containing a 23-E isomer of a 23-imino derivative of a LL-F28249 compound.

U.S. Pat. No. 4,988,824 describes a process for the preparation of 23-($C_1$-$C_6$alkyloxime)-LL-F28249 compounds and a method for purifying 23-($C_1$-$C_6$alkyloxime)-5-[(p-nitrobenzoyl)oxy]-LL-F28249 compounds. However, the process described in U.S. Pat. No. 4,988,824 occasionally produces product containing the 23-Z isomers of 23($C_1$-$C_6$alkyloxime)-LL-F28249 compounds and the purification procedure described therein does not separate the 23-Z isomer from the desired 23-E isomer.

It is therefore an object of the present invention to provide a method for the purification of 23-E isomers of 23-imino derivatives of LL-F28249 compounds which is less arduous, less time-consuming and more efficient than the methods known in the art.

SUMMARY OF THE INVENTION

The present invention provides a method for increasing the purity of the 23-E isomer of a 23-imino derivative of a LL-F28249 compound present in a first mixture which comprises reacting the first mixture comprising the 23-E isomer of the 23-imino derivative of the LL-F28249 compound having the structural formula I

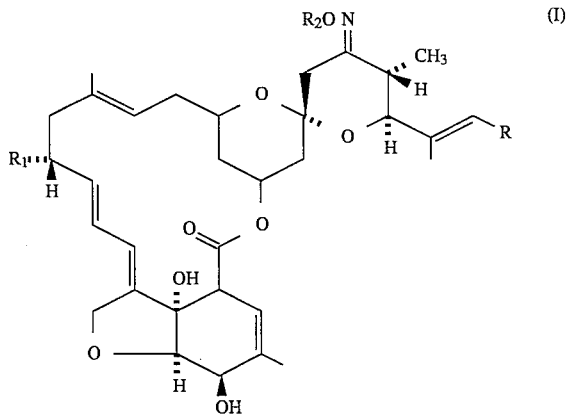

wherein

R is methyl, ethyl or isopropyl;

$R_1$ is hydrogen or methyl; and $R_2$ is $C_1$-$C_6$alkyl, $C_1$-$C_4$alkoxymethyl, benzyl, allyl, propargyl, phenyl, $CH_2CO_2$- ($C_1$-$C_4$alkyl), N-($C_1$-$C_6$alkyl) carbamoyl, N-(allyl) carbamoyl, N-(propargyl) carbamoyl, N-(phenyl) carbamoyl, N-(chlorophenyl)carbamoyl, N-(dichlorophenyl)carbamoyl, N-(benzyl)carbamoyl, $C_1$-$C_6$alkanoyl, chloroacetyl, methoxyacetyl, phenylacetyl optionally substituted on the phenyl ring with one or two halogen atoms, $C_1$-$C_4$alkyl groups, $C_1$-$C_4$alkoxy groups or nitro groups, phenoxyacetyl optionally substituted on the phenyl ring with one or two halogen atoms, $C_1$-$C_4$alkyl groups, $C_1$-$C_4$alkoxy groups or nitro groups, or benzoyl optionally substituted with one or two halogen atoms, $C_1$-$C_4$alkyl groups, $C_1$-$C_4$alkoxy groups or nitro groups, with a protecting agent and a base to form a second mixture comprising a solid compound having the structural formula

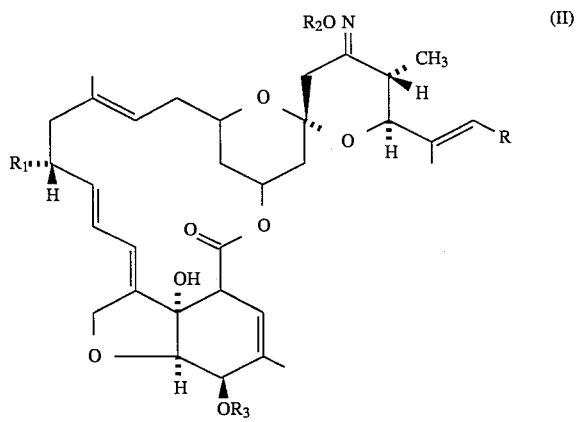

wherein R, $R_1$ and $R_2$ are as described above for formula I, and $R_3$ is a protecting group, mixing the second mixture with methanol, separating the formula II compound and deprotecting the formula II compound.

DETAILED DESCRIPTION OF THE INVENTION

The 23-E isomers of 23-imino derivatives of LL-F 28249 compounds are useful for preventing or controlling helminth, ectoparasite, insect, nematode and acarid infestations in human and animal health areas and in agriculture. Those compounds may be administered orally or parenterally for human and animal use. When preparing a formulation for human or animal use, it is highly desirable to use high purity technical material. However, the purities of technical materials containing 23-E isomers of 23-imino derivatives of LL-F28249 compounds are not always satisfactory. To increase the purities of those compounds, arduous and time-consuming methods are employed.

Advantageously, it has been discovered that the purity of the 23-E isomer of a 23-imino derivative of a LL-F28249 compound is increased by reacting a first mixture comprising the 23-E isomer of the 23-imino derivative of the LL-F28249 compound having the structural formula I

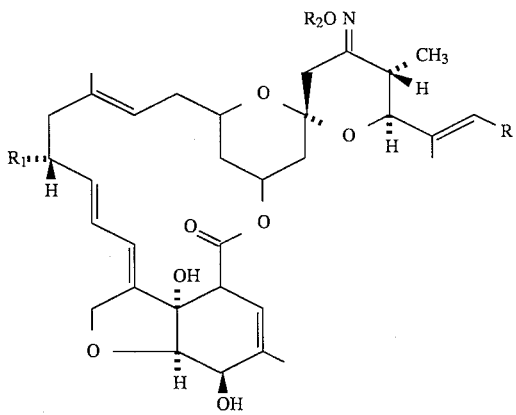

wherein R, $R_1$ and $R_2$ are as described above, with a protecting agent and a base to form a second mixture comprising a solid compound having the structural formula II

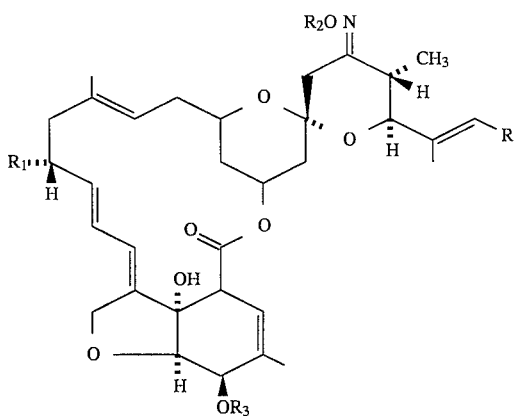

wherein R, $R_1$ and $R_2$ are as described above for formula I, and $R_3$ is a protecting group, mixing the second mixture with methanol, separating the formula II compound and deprotecting the formula II compound to obtain a third mixture having a higher purity of the formula I compound than the first mixture.

Uniquely, it has been found that the method of the present invention efficiently separates the 23-Z isomer of a 23-imino derivative of a LL-F28249 compound from the corresponding 23-E isomer of the compound. Further, the method of the invention is effective even in the presence of other components. Heretofore, such separation was achieved by complex, time-consuming procedures such as column chromatography.

The term protecting group as used in the specification and claims designates those groups well known in the art to block a hydroxyl functionality, for example, ester groups such as acetate, chloroacetate, dichloroacetate, trichloroacetate, trifluoroacetate, methoxyacetate, phenoxyacetate, benzoate, halobenzoate, nitrobenzoate and the like Preferred protecting groups for use in the method of this invention are ester groups such as benzoate, halobenzoate and nitrobenzoate.

Protecting agents suitable for use in the method of the present invention are those agents well known in the art to provide the protecting groups defined above. Preferred protecting agents are acid halides such as acetyl chloride, chloroacetyl chloride, dichloroacetyl chloride, trichloroacetyl chloride, trifluoroacetyl chloride, methoxyacetyl chloride, phenoxyacetyl chloride, benzoyl chloride, halobenzoyl chloride, nitrobenzoyl chloride and the like.

Preferred formula I compounds purified by the method of the present invention are those wherein R is methyl, ethyl or isopropyl;

$R_1$ is hydrogen or methyl; and $R_2$ is $C_1$–$C_6$alkyl, $C_1$–$C_4$alkoxymethyl, benzyl, allyl, propargyl or phenyl.

More preferred formula I compounds purified by the method of this invention are those wherein R is isopropyl;

$R_1$ is methyl; and $R_2$ is $C_1$–$C_6$alkyl.

The method of the present invention is especially useful for the purification of formula I compounds wherein R is isopropyl;

$R_1$ is methyl; and $R_2$ is methyl, when $R_3$ is p-nitrobenzoate.

Bases suitable for use in the method of this invention include organic bases such as tri($C_1$–$C_4$alkyl)amines, pyridine, 4-dimethylaminopyridine, imidazole and the like with tri($C_1$–$C_4$alkyl)amines such as triethylamine and trimethylamine being preferred.

Advantageously, it has been found that formula II compounds are insoluble in methanol and that impurities present in the second mixture are soluble in methanol. Therefore, by mixing the second mixture with methanol and separating the insoluble formula II compound, impurities are significantly reduced. The purified formula II compound is then deprotected to obtain the desired formula I compound in high purity.

The formula II compounds may be deprotected under basic conditions to obtain the formula I compounds. Bases suitable for use in the deprotection step include alkali metal hydroxides such as sodium hydroxide and potassium hydroxide, alkaline earth metal hydroxides and the like.

In order to facilitate a further understanding of the invention, the following examples are presented to illustrate more specific details thereof. The invention is not to be limited

EXAMPLE 1
Preparation of 23-(O-Methyloxime)-5-[(p-nitrobenzoyl)oxy]-LL-F28249alpha, 23-E isomer

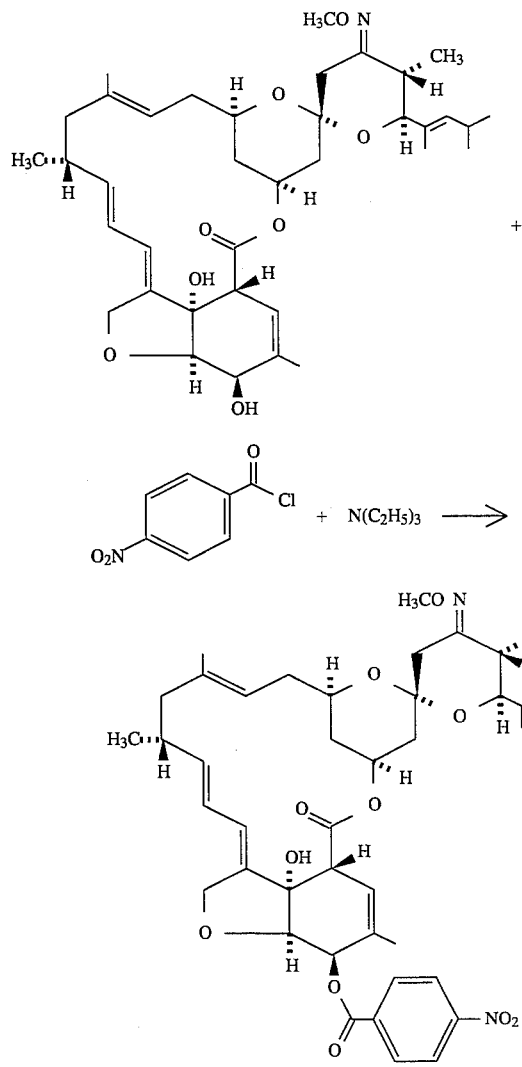

A solution of 23-(O-methyloxime)-LL-F28249alpha, 23-E isomer (8.57 g, 90.9% real, 12.18 mmol real) and triethylamine (3.1 g, 30.63 mmol) in toluene is cooled to 10°–15° C., treated portionwise with p-nitrobenzoyl chloride (4.97 g, 26.78 mmol), diluted with additional toluene, stirred for 19 hours, treated with additional triethylamine (0.41 g, 4.05 mmol) and p-nitrobenzoyl chloride (0.74 g, 3.99 mmol), stirred for 5 hours, treated with additional triethylamine (0.41 g, 4.05 mmol) and p-nitrobenzoyl chloride (0.74 g, 3.99 mmol), stirred for 2 hours, treated with additional triethylamine (0.2 g, 1.98 mmol) and p-nitrobenzoyl chloride (0.37 g, 1.99 mmol), stirred for 30 minutes and filtered to obtain a clear yellow filtrate. The filtrate is washed sequentially with 6% sodium hydrogen carbonate solution, 10% hydrochloric acid and water and concentrated in vacuo to give a yellow slurry (23.6 g). Butanol (58 g) is added to the slurry and the resultant mixture is vacuum distilled to remove toluene. Methanol (71 g) is added to the distilled mixture and the methanol mixture is stirred at 65°–70° C. for 1 hour, cooled to 40°–50° C., stirred at 50°–55° C. for 15 minutes, cooled to 15°–20° C. and filtered to obtain a filter cake. The filter cake is washed with methanol and dried in a vacuum oven at 35°–45° C. with a nitrogen bleed to give the title product as a solid (9.05 g, 97.5% real, 91.9% yield).

EXAMPLE 2
Preparation of purified 23-(O-Methyloxime)-LL-F28249alpha, 23-E isomer

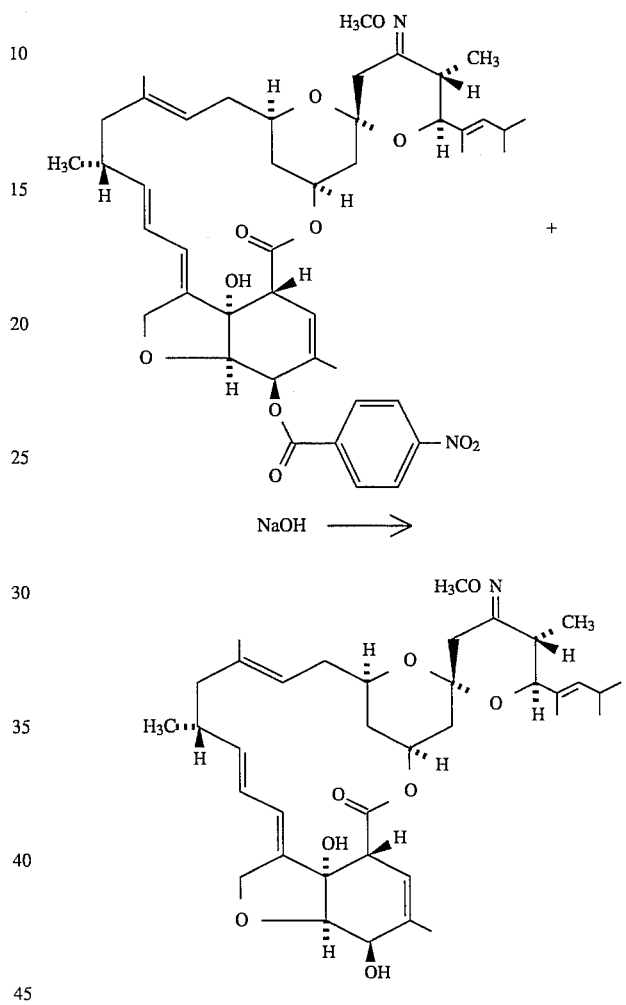

A 4% sodium hydroxide solution (1.52 g) is added to a solution of 23-(O-methyloxime)-5-[(p-nitrobenzoyl)oxy]-LL-F28249alpha, 23-E isomer (1.0 g from the product of Example 1) in p-dioxane (10 g) and allyl alcohol (0.18 g) at 5°–10° C. The reaction mixture is stirred at 5°–10° C. for 4.5 hours and diluted with water and methylcyclohexane. The organic phase is separated, washed sequentially with water and a 5% magnesium sulfate solution (7.4 g) and concentrated in vacuo to obtain a white foam. A mixture of the foam and methanol is distilled to remove residual methylcyclohexane and p-dioxane. The distilled mixture is added to a 0.5% magnesium sulfate solution. The resultant mixture is stirred for 20 minutes and filtered to obtain a solid which is washed with water and dried in a vacuum oven at 35°–45° C. with a nitrogen bleed to give the title product as a solid (0.77 g, 93.8% pure).

As can be seen from Examples 1 and 2, the purity of 23-(O-methyloxime)-LL-F28249alpha, 23-E isomer is increased from 90.9% to 93.8%.

Using essentially the same procedure described in Examples 1 and 2, the purity of a mixture containing 76% 23-(O-methyloxime)-LL-F28249alpha, 23-E isomer and 19% 23-(O-methyloxime)-LL-F28249alpha, 23-Z isomer is increased to 91.9% 23-(O-methyloxime)-LL-F28249alpha, 23-E isomer and the amount of 23-(O-methyloxime)-LL-F28249alpha, 23-Z isomer is reduced to less than 0.5%.

I claim:

1. A method for increasing the purity of the 23-E isomer of a 23-imino derivative of a LL-F28249 a compound present in a first mixture which comprises reacting the first mixture comprising the 23-E isomer of the 23-imino derivative of the LL-F28249 a compound having the structural formula I

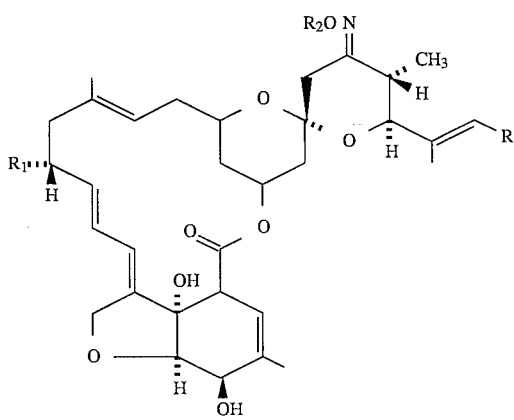

wherein

R is methyl, ethyl or isopropyl;

$R_1$ is hydrogen or methyl; and $R_2$ is $C_1$–$C_6$alkyl, $C_1$–$C_4$alkoxymethyl, benzyl, allyl, propargyl, phenyl, $CH_2CO2$-($C_1$–$C_4$alkyl), N-($C_1$–$C_6$alkyl)carbamoyl, N-(allyl)carbamoyl, N-(propargyl)carbamoyl, N-(phenyl)carbamoyl, N-(chlorophenyl)carbamoyl, N-(dichlorophenyl)carbamoyl, N-(benzyl)carbamoyl, $C_1$–$C_6$alkanoyl, chloroacetyl, methoxyacetyl, phenylacetyl optionally substituted on the phenyl ring with one or two halogen atoms, $C_1$–$C_4$alkyl groups, $C_1$–$C_4$alkoxy groups or nitro groups, phenoxyacetyl optionally substituted on the phenyl ring with one or two halogen atoms, $C_1$–$C_4$alkyl groups, $C_1$–$C_4$alkoxy groups or nitro groups, or benzoyl optionally substituted with one or two halogen atoms, $C_1$–$C_4$alkyl groups, $C_1$–$C_4$alkoxy groups or nitro groups, with a protecting agent and a base to form a second mixture comprising a solid compound having the structural formula II

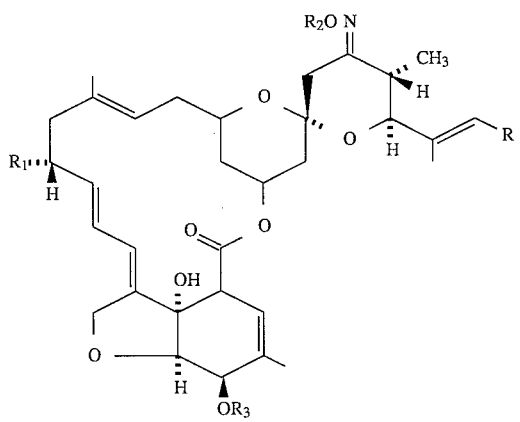

wherein R, $R_1$ and $R_2$ are as described above for formula I, and $R_3$ is a protecting group, mixing the second mixture with methanol, separating the formula II compound and deprotecting the formula II compound.

2. The method according to claim 1 wherein the first mixture further comprises the 23-Z isomer of the compound of formula I.

3. The method according to claim 1 wherein $R_3$ is an ester group.

4. The method according to claim 3 wherein

R is methyl, ethyl or isopropyl;

$R_1$ is hydrogen or methyl;

$R_2$ is $C_1$–$C_6$alkyl, $C_1$–$C_4$alkoxymethyl, benzyl, allyl, propargyl or phenyl; and $R_3$ is benzoate, halobenzoate or nitrobenzoate.

5. The method according to claim 4 wherein

R is isopropyl;

$R_1$ is methyl;

$R_2$ is $C_1$–$C_6$alkyl; and $R_3$ is benzoate, halobenzoate or nitrobenzoate.

6. The method according to claim 5 wherein

R is isopropyl;

$R_1$ is methyl;

$R_2$ is methyl; and $R_3$ is p-nitrobenzoate.

7. The method according to claim 1 wherein the base is selected from the group consisting of a tri($C_1$–$C_4$alkyl)amine, pyridine, 4-dimethylaminopyridine, and imidazole.

8. The method according to claim 7 wherein the base is a tri($C_1$–$C_4$alkyl)amine.

9. The method according to claim 1 wherein the formula II compound is deprotected with a base.

10. The method according to claim 1 wherein the protecting agent is an acid halide.

11. The method according to claim 10 wherein the protecting agent is selected from the group consisting of acetyl chloride, chloroacetyl chloride, dichloroacetyl chloride, trichloroacetyl chloride, trifluoroacetyl chloride, methoxyacetyl chloride, phenoxyacetyl chloride, benzoyl chloride, halobenzoyl chloride, nitrobenzoyl chloride.

12. The method according to claim 11 wherein the protecting agent is p-nitrobenzoyl chloride.

13. A method for increasing the purity of the 23-E isomer of a 23-imino derivative of a LL-F28249 a compound present in a first mixture which comprises reacting the first mixture comprising the 23-E isomer of the 23-imino derivative of the LL-F28249 a compound having the structural formula I

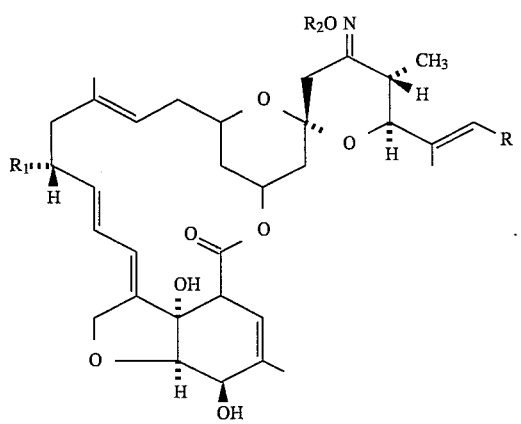

(I)

wherein

R is methyl, ethyl or isopropyl;

$R_1$ is hydrogen or methyl; and $R_2$ is $C_1$–$C_6$alkyl, $C_1$–$C_4$alkoxymethyl, benzyl, allyl, propargyl or phenyl with a protecting agent and a base to form a second mixture comprising a solid compound having the structural formula II

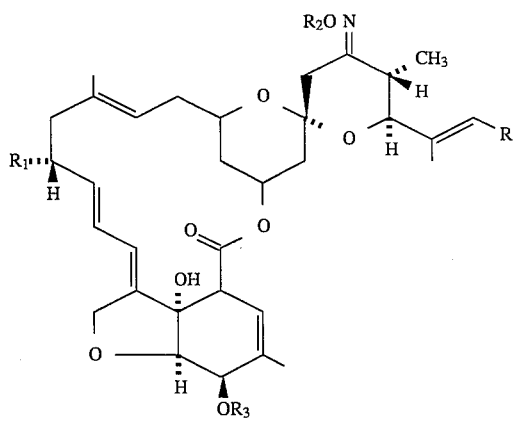

(II)

wherein R, $R_1$ and $R_2$ are as described above for formula I, and $R_3$ is a protecting group, mixing the second mixture with methanol, separating the formula II compound and deprotecting the formula II compound.

14. The method according to claim 13 wherein the base is triethylamine and the protecting agent is p-nitrobenzoyl chloride.

15. The method according to claim 14 wherein the first mixture further comprises the 23-Z isomer of the compound of formula I.

16. A method for increasing the purity of the 23-E isomer of a 23-imino derivative of a LL-F28249 a compound present in a first mixture which comprises reacting the first mixture comprising the 23-E isomer of the 23-imino derivative of the LL-F28249 a compound having the structural formula I

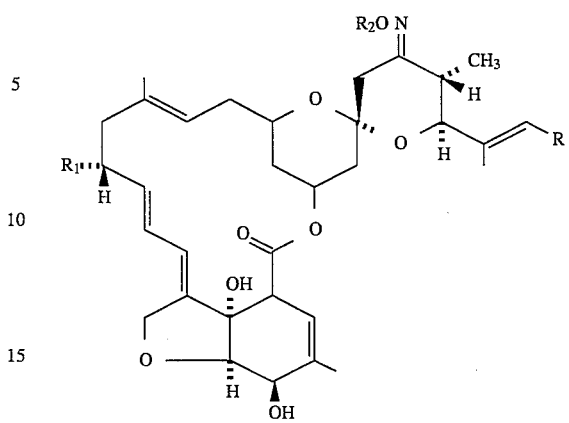

(I)

wherein

R is isopropyl;

$R_1$ is methyl; and $R_2$ is methyl, with p-nitrobenzoyl chloride and triethylamine to form a second mixture comprising a solid compound having the structural formula II (II)

wherein R, $R_1$ and $R_2$ are as described above for formula I, and $R_3$ is p-nitrobenzoate, mixing the second mixture with methanol, separating the formula II compound and deprotecting the formula II compound.

17. The method according to claim 16 wherein the formula II compound is deprotected with a base selected from the group consisting of sodium hydroxide and potassium hydroxide.

18. The method according to claim 17 wherein the first mixture further comprises the 23-Z isomer of the compound of formula I.

* * * * *

UNITED STATES PATENT AND TRADEMARK OFFICE
CERTIFICATE OF CORRECTION

PATENT NO. : 5,478,951
DATED : December 26, 1995
INVENTOR(S) : Kenneth A. M. Kremer It is certified that error appears in the above-identified patent and that said Letters Patent are hereby corrected as shown below:

Column 7, lines 7 and 10 after "LL-F28249 insert -- ∝ --
Column 8, lines 61 and 65 after "LL-F28249" insert -- ∝ --
Column 9, lines 55 and 58 after "LL-28249" insert -- ∝ --

Signed and Sealed this

Third Day of April, 2001

Attest:

NICHOLAS P. GODICI

Attesting Officer      Acting Director of the United States Patent and Trademark Office